(12) United States Patent
Nagasaki et al.

(10) Patent No.: US 7,642,343 B2
(45) Date of Patent: Jan. 5, 2010

(54) PEG-FUNCTIONAL NUCLEIC ACID CONJUGATE

(75) Inventors: Yukio Nagasaki, Moriya (JP); Kazunori Kataoka, Tokyo (JP); Shigeki Sasaki, Koga (JP); Fumi Nagatsugi, Sendai (JP); Motoi Oishi, Tsukuba (JP)

(73) Assignee: Japan Science and Technology Agency, Saitama (JP)

( * ) Notice: Subject to any disclaimer, the term of this patent is extended or adjusted under 35 U.S.C. 154(b) by 316 days.

(21) Appl. No.: 11/578,560

(22) PCT Filed: Apr. 14, 2005

(86) PCT No.: PCT/JP2005/007568

§ 371 (c)(1),
(2), (4) Date: Oct. 16, 2006

(87) PCT Pub. No.: WO2005/100447

PCT Pub. Date: Oct. 27, 2005

(65) Prior Publication Data

US 2008/0097087 A1 Apr. 24, 2008

(30) Foreign Application Priority Data

Apr. 16, 2004 (JP) ............................. 2004-122124

(51) Int. Cl.
*C07H 21/00* (2006.01)
*C07H 21/02* (2006.01)
*C12Q 1/68* (2006.01)

(52) U.S. Cl. ................... 536/23.1; 536/24.3; 536/24.33; 435/6

(58) Field of Classification Search ................ 536/23.1, 536/24.3, 24.33; 435/6
See application file for complete search history.

(56) References Cited

U.S. PATENT DOCUMENTS 6,558,658 B2 * 5/2003 Harris ....................... 424/78.3
2003/0191074 A1 10/2003 Segev

FOREIGN PATENT DOCUMENTS

| JP | 2001-206896 | 7/2001 |
|----|-------------|--------|
| JP | 2004-250537 | 9/2004 |
| WO | 01/37879 | 5/2001 |
| WO | 02/061110 | 8/2002 |

* cited by examiner

*Primary Examiner*—Jezia Riley
(74) *Attorney, Agent, or Firm*—Wenderoth, Lind & Ponack, L.L.P.

(57) ABSTRACT

The invention provides a conjugate of functional oligonucleotide with poly(ethylene oxide), polyion complex of the conjugate with cationic polymer, and micelle thereof. The micelle improves stability of the oligonucleotide in animal cells and its specific bindability to target gene.

14 Claims, 3 Drawing Sheets

PEG-FUNCTIONAL NUCLEIC ACID CONJUGATE

TECHNICAL FIELD

This invention relates of oligonucleotide derivatives which are useful in the fields of biochemistry and pharmaceutics. More specifically, the invention relates to conjugates of oligonucleotides, which can stably exist in physiological environments and furthermore are capable of hybridizing with nucleotide sequences of certain specific target genes, with poly(ethylene oxide); and also to polyion complexes of the conjugates.

BACKGROUND ART

As carriers for delivering genes to their target regions within the living body, in addition to modified retrovirus, modified adenovirus and the like, use of synthetic carriers, e.g., cationic liposome, membrane fusion liposome, polycation (for example, DEAE-dextran, poly-L-lysine, chitosan), polycation-containing block copolymer and the like has been investigated, from the viewpoint of safety. In particular, a DNA delivery system utilizing a polyion complex micelle (PIC micelle) proposed by some of the present inventors represented by Kataoka is a promising delivery system as it generally exhibits good drug-encapsulating micelle stability, migratability into target cells or tissues, and drug stability in the tissues (see, for example, the later-listed non-patent reference 1). However, in a system which uses antisense oligonucleotide to certain specific target genes for controlling their expression, occasionally it is difficult to stably maintain an oligonucleotide having relatively small molecular weight in PIC micelle, even when the above PIC micelle is used.

Some of the present inventors discovered that oligonucleotide could be retained in PIC micelle with relatively good stability, when it was covalently bonded with poly(ethylene oxide) to form a conjugate and thereafter used to form PIC micelle with polycation. They have also succeeded in integrating, in the occasion of forming the conjugate, in the linkage moiety an ester bond which is cleavable under physiological environments, in particular, at pH of endosome (=5.5) and disclosed it to the public (e.g., see the following non-patent reference 2). The oligonucleotide thus encapsulated in PIC micelle also exhibits resistance to action of nuclease in vitro.

On the other hand, as oligonucleotide derivatives which themselves are resistant to nuclease, phosphorothioate oligonucleotide (e.g., see the following non-patent reference 3), phosphoroamidate oligonucleotide (see, the following non-patent reference 4) and 2'-O-methylphosphate oligonucleotide (see, the following non-patent reference 5) have been synthesized, some of which are being given clinical tests with the view to establish gene therapy. Also for the purpose of unfailingly suppressing expression of target genes in gene therapy, a functional oligonucleotide in which a group of the formula —CH$_2$CH$_2$S(O)nPh (wherein n stands for an integer of 0-2) (a precursor of vinyl group) is introduced at 6-position of its 2-aminopurine ring to allow its crosslinkage with a specific target gene by covalent bond has been proposed (see, the following non-patent reference 6 or patent reference 1). It is also specifically shown that such a functional oligonucleotide is crosslinkable in vitro with amino group of cytosine of the other oligonucleotide of complementary sequence, by means of covalent bond, making use of the vinyl group precursor.

LIST OF CITED REFERENCES

Patent reference 1: JP 2001-206896A
Non-patent reference 1: Kataoka et al. *Macromolecules*, 29 (1996) 8556-8557
Non-patent reference 2: Oishi et al. *Biomacromolecules*, 2003, 4, 1426-1432
Non-patent reference 3: Stepkowski et al. *J. Immunol.*, 153 (1994) 5336-5346
Non-patent reference 4: Barak et al. *Biochemistry*, 2000, 39,
Non-patent reference 5: Lesnik et al. *Biochemistry* 1998, 37, 6991-6997
Non-patent reference 6: Nagatsugi et al. *J. Am. Chem. Soc.* 1999, 121, 6753-6754

DISCLOSURE OF THE INVENTION

Above-described oligonucleotide and PIC micelle succeeded in enhancing resistance of the oligonucleotide (inclusive of the functional oligonucleotide) to nuclease or in forming strong bond between the oligonucleotide and the target gene. However, it is still necessary to provide functional oligonucleotide exhibiting even more increased resistance to nuclease and being capable of binding to target gene in specific organ or cell of living body, or a delivery system of such oligonucleotide. The present invention meets such needs.

The present inventors discovered that a PIC micelle encapsulating a conjugate of a certain specific oligonucleotide (see, non-patent reference 2) with poly(ethylene oxide) could be effectively taken into animal cells and furthermore could potently inhibit expression of target genes. They also discovered: when those functional oligonucleotides disclosed in non-patent references 3 and 4 were used to form conjugates with poly(ethylene oxide) and converted to PIC micelles with polycation, they could be stably and effectively delivered into animal cells and furthermore could inhibit expression of target genes.

It is moreover found that these conjugates exhibit very high mobility in aqueous media, and specifically bind to target genes (via hydrogen bond or the like) although their highly hydrophilic poly(ethylene oxide) chains are covalently bonded to the oligonucleotide chains. Still in addition, such conjugates of the functional oligonucleotides (see, non-patent reference 4) with poly(ethylene oxide) are found to achieve surprising functional effect to inhibit expression of target genes significantly more potently than conjugates using non-functional oligonucleotides. Although no theoretical binding is intended, the reason for this potent inhibition is considered to be that the conjugate enables the functional oligonucleotide's specific access to target gene and furthermore the vinyl group on the functional oligonucleotide and the amino group on cytidine in the target gene form a covalent bond.

Therefore, according to the present invention, a conjugate of oligonucleotide, which is useful in a system for inhibiting expression of certain specific genes is provided. Specifically, the invention provides a conjugate of oligonucleotide with poly(ethylene oxide) which is expressed by a general formula (A):

$$\text{FuNT-L}_1\text{-L}_2\text{-PEG} \quad\quad\quad (A)$$

in which FuNT stands for the residue of a functional oligonucleotide bound to L$_1$-L$_2$-PEG via a phosphate ester bond at 3' or 5' hydroxyl terminal of ribose or 2-deoxyribose, wherein the functional oligonucleotide a) is composed of an oligonucleotide sequence which either is complementary to the nucleotide sequence participating in expression of target genes, or hybridizes with the nucleotide sequence under stringent condition; and which has, at 6-position of at least one 2-aminopurine ring present in the oligonucleotide sequence, a group of the formula —$CH_2CH_2S(O)nR$ (wherein n stands for an integer of 0-2; and R stands for $C_1$-$C_6$ alkyl optionally substituted with oxy (=O), cyano or carboxy; or phenyl optionally substituted with oxy (=O), cyano, nitro, carboxy, $C_1$-$C_6$ alkyl or halo); or b) is complementary to the nucleotide sequence participating in expression of the target genes and the phosphate moiety of each nucleotide therein is selected from the group consisting of phosphorothioate, phosphoroamidate and 2'-O-methylphosphate;

$L_1$ stands for an alkylene group of 3-30 in total atom number, which may be interrupted with oxygen atom or sulfur atom at one, two or more places;

$L_2$ is a linking group cleavable under physiological conditions; and

PEG stands for poly(ethylene oxide) group carrying at the $L_2$-binding terminal hydrogen atom, alkyl group, aralkyl group, functional group or ligand residue, optionally via a linking group.

According to the present invention, furthermore, a polyion complex (PIC) of the conjugate with a polymer containing polycationic segment(s) is provided.

Hereinafter the invention is described more specifically.

The conjugate and polyion complex according to the invention mainly aim at inhibiting expression of certain specific target genes. Therefore, the functional oligonucleotide contains a sequence which is either complementary to the nucleotide sequence which participates in expression of the specific genes (or target genes), or a sequence which hybridizes with, under stringent condition, the nucleotide sequence participating in expression of the specific genes. The nucleotide sequence participating in expression of target genes relevant to the present invention includes specific coding sequences and also such genes or gene domains which participate in transcription or translation of the coding sequences. Examples of sequences which are complementary to these sequences (generally, antisense oligonucleotide) include, although not limited thereto, those which inhibit transcription of target genes, RNA processing, migration of mRNA from nuclei and translation.

In particular, those functional oligonucleotides classifiable under a) above have at least one functional nucleotide unit of a formula (B):

(B)

(in which n stands for an integer of 0-2; and R stands for a $C_1$-$C_6$ alkyl (e.g., methyl, ethyl. n-propyl, iso-propyl and the like) which is optionally substituted with oxy (=O), cyano (—CN), nitro, or carboxy, or phenyl which is optionally substituted with oxy, nitro, carboxy, $C_1$-$C_6$ alkyl (e.g., methyl) or halo (e.g., fluorine, chlorine))

in their oligonucleotide sequence, and can form a covalent bond with the amino group (—$NH_2$) of cytosine in complementary oligonucleotide sequence of target genes, making use of —$CH_2CH_2S(O)_nR$ group in the unit. The functional nucleotide unit(s) may be present at any position(s) in the functional oligonucleotide chain. Such a covalent bond is understood as being formed as —$CH_2CH_2S(O)_mR$ is converted to —$CH_2=CH_2$ and then reacts with the amino group, when the target gene and the functional oligonucleotide contact with each other in an aqueous medium or physiological environments.

Whereas, even when a nucleotide sequence in a functional oligonucleotide is not necessarily completely complementary to specific nucleotide sequence of target genes, so long as it can be hybridized with the genes under stringent condition (for example, see "Molecular Cloning", 2nd ed. Gold Spring Harbor Laboratory, 1989, New York, 1.101-1.104), the sequence-specific linkage can be formed, and such functional oligonucleotides are also within the scope of the present invention.

On the other hand, functional oligonucleotides classified under b) above are those in which the phosphate bonds of the nucleotides are induced to phosphorothioate, phosphoroamidate and 2'-O-methylphosphate, as expressed respectively by the formulae (C)-(E):

The term, oligonucleotide, as used in the present invention signifies, not limited to those formed of several to ten-odd number of nucleotides as the term, "oligo" signifies, but includes those formed of at the maximum 200 nucleotides. Whereas, as oligodeoxynucleotide, those containing 10-50 nucleotides are preferred.

Direction of phosphodiester bond between any two nucleotides is normally 3'→5' or 5'→3'. Depending on the kind of the nucleotides, however, it may be 2'→5' or 5'→2', or these binding modes may be mixedly present. Furthermore, nucleotides constituting an oligonucleotide may be constituents of either DNA or RNA.

Such an oligonucleotide is covalently bonded, based on the normal directioning of DNA and RNA, with a group expressed by the formula, —$L_1$-$L_2$-PEG to form a phosphate ester bond via the 3' hydroxyl group at 3' terminal side (i.e., 5' position of ribose or 2-deoxyribose participates in phosphate diester bond) or the 5' hydroxyl group at 5' terminal side (i.e., 3' position of ribose or 2-deoxyribose participates in phosphate diester bond).

In the formula, $L_1$ can be alkylene group of total 3-30 in atom number which may be interrupted with oxygen or sulfur atom, or —NHCO—, preferably with oxygen atom, at 1, 2 or more places. Such an alkylene group may be branched, and hence can be any of the following, but not limited thereto:

—$CH_2CH_2CH_2$—,    —$CH_2(CH_3)CH$—,    —$CH_2(CH_2)_2CH_2$—,

—$CH_2CH_2$—O—$CH_2CH_2$—,    —$CH_2CH_2$—S—$CH_2CH_2$—,

—$CH_2CH_2$-($OCH_2CH_2$-$)_2$,

—$CH_2CH(CH_2OH)CH_2CH_2CH_2CH_2NHCOCH_2CH_2$—.

$L_2$ stands for a linking group which can be any group capable of linking FuNT-$L_1$ moiety and PEG moiety, as long as it suits the purpose of the present invention. For example, it may be one or more groups selected from alkylene (see, the above-named examples), allylene, —O—, —S—, —NH—, —COO—, —SS—, —NHCO—, —NHCO—NH— and —SO—. Although not limited thereto, as examples of $L_2$, —SS—, —$SCH_2CH_2$—COO—, —$OCH_2CH_2COO$—, —$NHCH_2CH_2COO$—, —$SCH_2CH_2$—$COOCH_2$— and —$SOCH_2CH_2COO$— can be named. Of such linking groups, those containing at least one group which is cleavable under physiological conditions (in the presence of peptidase, esterase, reducing substances and the like which are present in animal tissues, cells, humor and the like), for example, —SS—, —COO— or —OCO—, within the linking moiety are preferred. In particular, those containing one linking moiety which is cleavable at the pH of endosome (=5.5) are preferred.

In the formula, -PEG stands for poly(ethylene oxide) group carrying hydrogen, alkyl, aralkyl, functional group or ligand residue at the unbound terminal (the other terminal than the binding terminal to $L_2$), optionally via a linking group. More specifically, -PEG is a poly(ethylene oxide) represented by a formula (F):

—($CH_2CH_2O)_n$—$L_3$—X    (F)

in the formula, $L_3$ is single bond or a linking group selected from those alkylene or linking groups as defined for $L_1$ or $L_2$ in the above,

X is hydrogen; or a functional group selected from the group consisting of alkyl (e.g., methyl, ethyl, propyl, butyl, hexyl and the like), aralkyl (e.g., benzyl, phenethyl and the like), hydroxyl, aldehyde (or formyl: —CHO), acetalized formyl, amino, protected amino, maleimide, carboxyl and protected carboxyl (while the protective groups used for the protection signify, although not limited thereto, those protective groups for amino and carboxyl groups customarily used in peptide synthesis); or residue of ligand (e.g., sugar, biotin, hapten, hormone, enzyme substrate and the like) which is bound via such a functional group as above-named, and n is an integer of 5-500.

Poly(ethylene oxide) derivatives which give the poly(ethylene oxide) group of the formula (F) or —$L_2$—($CH_2CH_2O)_n$—$L_3$—X can be prepared following the poly(ethylene oxide) segment formation which is an intermediate stage for preparing the heterotelechelic hydrophilic-hydrophobic block copolymer which was proposed by some of the present inventors (for example, see WO 96/33233, WO96/32434, WO97/06202, earlier identified patent references 1 and 2) or, where necessary, by adding thereto techniques well known in the concerned art.

A typical preparation method of poly(ethylene oxide) derivatives can be carried our following the reaction schemes shown below, although not limited thereto.

Scheme 1:

Scheme 2:

(e)

Concerning the conditions of each of the reaction stages shown in the above reaction schemes, the patent reference 1 can be referred to.

Conjugates of oligonucleotides having —SS— bond or —COO— bond as $L_2$ in the general formula (A) with poly (ethylene oxide) can be prepared, for example, according to the following reaction schemes:

Scheme 3:

(f)

Scheme 4:

(g)

In the above formulae, oligo-FuNT can be those which are classified under a) and b) as defined as to the functional oligonucleotides.

Those classified under a) are obtainable based on those methods disclosed in non-patent reference 4 or patent reference 1, and those classified under b), based on the method disclosed in non-patent reference 3. For preparation of oligo-FuNT-CH$_2$CH$_2$CH$_2$SH, the method as described in non-patent reference 2 can be referred to.

Genes targeted by those functional oligonucleotides of the present invention can be any that suit for the purpose of the invention, which preferably can be pathogenic genes of animals and DNA or RNA portions participating in their expression. Although not limited thereto, as examples of target genes PKCα associated with non-small cell lung cancer, BCL-2 associated with malignant melanoma, ICAM-1 associated with clonal disease, HCV associated with hepatitis C, TNFα associated with rheumarthritis and lepra, adenosine A1 receptor associated with asthma, c-rafkinase associated with ovary cancer, H-ras associated with pancreas cancer, c-myc associated with coronary disease cancer, PKA RIα associated with colon cancer, HIV associated with AIDS, DNA methyltransferase associated with solid cancer, VEGF receptor associated with cancer, ribonucleotide reductase associated with kidney cancer, CMV IE2 associated with CMV-retinitis, MMP-9 associated with prostatic cancer, TGFβ2 associated with malignant glioma, CD49d associated with multiple sclerosis, PTP-1B associated with diabetes, c-myb associated with cancer, EGFR associated with mammary cancer, mdr1 and GLUT-1 which are associated with cancer can be named.

As antisense sequences capable of effectively inhibiting expression of these genes, those known per se can be utilized.

Thus obtained conjugates according to the present invention may be further subjected to a ligand-adding reaction, where necessary. For example, it is also possible to introduce a ligand by acid hydrolyzing acetalized formyl group [(CH$_3$CH$_2$O)CH—] of a conjugate expressed by above (f) or (g) to convert it to formyl group (—CHO), and then introducing amino group, where necessary, or reacting the conjugate with a ligand carrying an amino group.

These conjugates form PIC with polymers containing polycationic segments, in an aqueous medium (e.g., buffered physiological saline or the like) and can automatically associate (or self-assemble) to form PIC micelles. Such PIC or PIC micelles also are embodiments of the present invention. According to the present invention, as polymers containing polycationic segments, homopolymers whose polycationic segments are selected from the group consisting of polylysine, polyethyleneimine, poly(di-C$_{1-3}$ alkylaminoethyl) methacrylate, oligoarginine, tat and KALA; and block copolymers containing these polycationic segments and poly (ethylene oxide) segments can be used.

Some of these polymers are available on the market, which can be used as they are, or those prepared by referring to non-patent reference 1 and the like can be used.

Above PIC micelles can stably retain therein conjugates of functional oligonucleotides with poly(ethylene oxide) even in dilute aqueous solution. The PIC micelles can furthermore be effectively taken into animal cells, and can release the functional oligonucleotides as cleaved from the conjugates under the environments of pH (=5.5) of endosome. Still in addition, functional oligonucleotides classified under a) are sequence-specifically crosslinkable with target genes via formation of covalent bond, and therefore can inhibit expression of the genes with higher certainty. Hence the PIC micelles are useful for inhibiting expression of genes in in vitro, ex-vivo and in vivo systems and are also useful in the field of gene therapy.

BRIEF EXPLANATION OF DRAWINGS

FIG. 1 *a*) is a chart indicating the HPLC change (at 0 hr. and after 4 hrs.) in a reaction of PEG with a functional oligonucleotide, and FIG. 1 *b*) shows MALDI-TOF-MS spectrum of PEG-modified oligonucleotide conjugate (2-carboxyphenyl sulfide compound).

FIG. 2 is a graph showing the results of antisense effect of the conjugate and of the PIC micelle encapsulating the conjugate according to the present invention, in which the axis of ordinates shows representation of firefly luciferase/representation of sea kidney luciferase (%). As for (1)-(12) on the axis of abscissae, Example 2 is to be referred to.

Hereinafter the present invention is further explained, referring to specific examples.

REFERENTIAL PRODUCTION EXAMPLE 1

Preparation of Acetal-PEO-Acrylate

In an eggplant type flask, under argon atmosphere at room temperature, 1.0 mmol (0.16 mL) of initiator 3,3-diethoxy-1-propanol was added to 25 ml of solvent tetrahydrofuran (THF) with microsyringe, and further 1.0 mmol (0.325 mol/liter-THF solution, 3.1 mL) of K-naphthalene was added to effect metallization for 10 minutes. Then 110 mmols (5.5 mL) of ethylene oxide was added, and stirred for two days under cooling with ice, to effect anionic ring-opening polymerization. Thereafter three molar times of triethylamine, 3.0 mmols (0.42 mL) and three molar times of acryloyl chloride, 3.0 mmols (0.24 mL) as a terminating agent were added by the order stated, and the termination reaction was carried out at room temperature for a day. The reaction product was subsequently purified by the steps of 2-propanol precipitation (2 liters), centrifugal separation (5000×g, 45 minutes), reduced pressure drying and benzene lyophilization. The yield of the product was 5.0 g (98%).

Thus obtained polymer was confirmed to be of mono peak type and have a number-average molecular weight of 4830 which approximately coincided with the molecular weight of the feed, 5080, by gel permeation chromatography measurement.

Similarly, in the measurement with MALDI-TOF-MS (Matrix-aided Laser Deionizing-Time-Of-Flight-Mass Spectrometer), the produced polymer was found to be mono peak type and have a number-average molecular weight of 4460. Upon comparing the measured values and calculated values of these peaks, it was confirmed that the polymer was a heterotelechelic polyethylene oxide with main chain of ethylene oxide skeletal structure, having acetal group at its α-terminal and acrylate group at its ω-terminal.

Furthermore, the average molecular weight of this polymer was calculated to be 4870, from $^1$H-NMR (proton nuclear magnetic resonance) spectrum in $d_6$-DMSO. The polymer was again confirmed to be a heterotelechelic polyethylene oxide with main chain of ethylene oxide skeletal structure, having acetal group at its α-terminal and acrylate group at its ω-terminal.

EXAMPLE 1

Preparation of Acetal-PEG-Functional Oligonucleotide Conjugate in the above formula, X is a deoxynucleotide derivative residue represented by one of the following formulae:

antisense DNA

Figure 1:
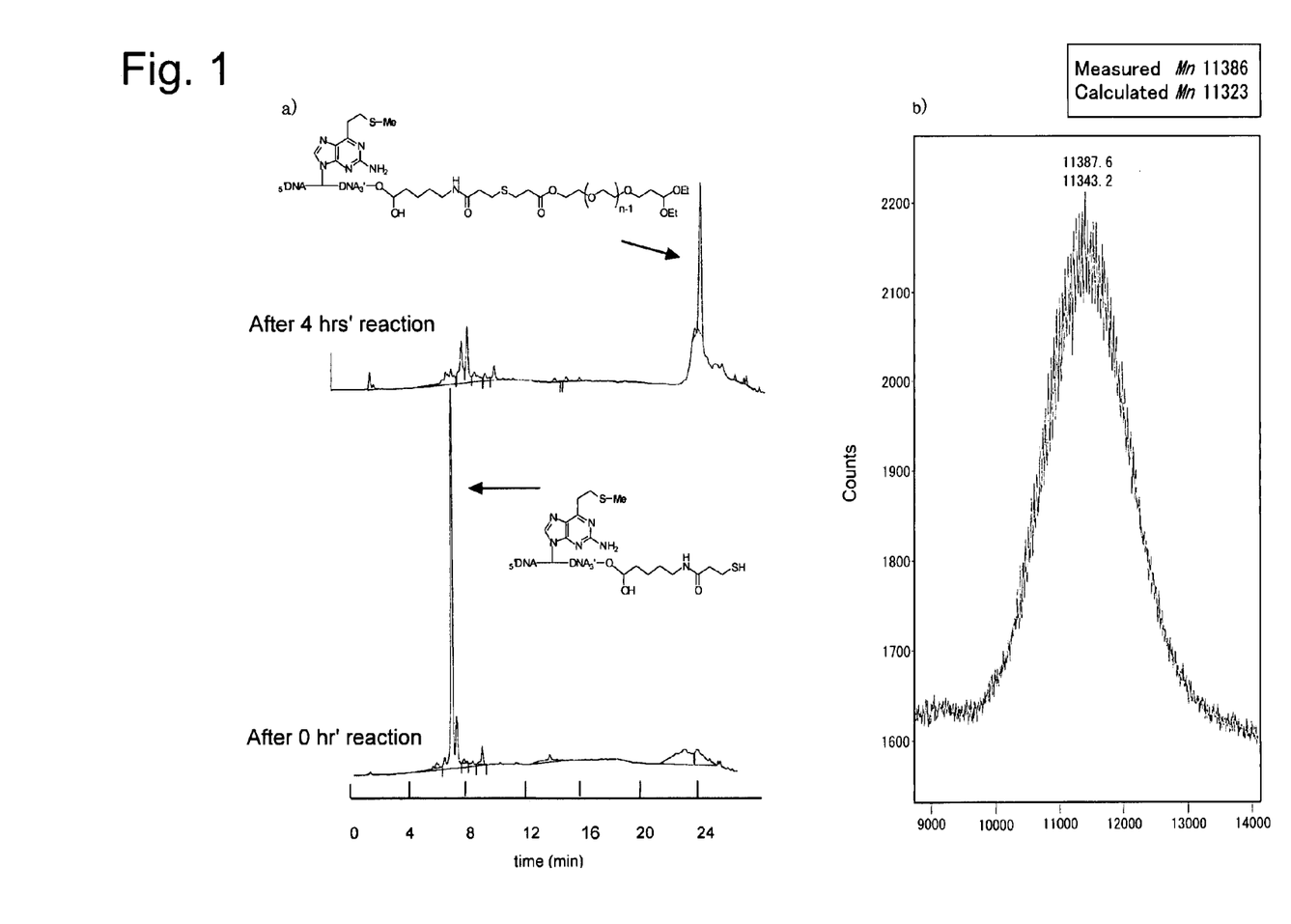

Using an amidite precursor of 2-amino-6-vinylpurine, 3'-terminal amino oligomer containing 2-amino-6-vinylpurine was synthesized. This oligomer (0.5 μmol) was oxidized with 1.5 μmols of magnesium monoperphthalate (MMPP). Successively the reaction liquid was rendered alkaline (pH 10) to effectively synthesize a 3' terminal amino oligomer having a vinyl group. This oligomer (0.5 μmol) was reacted with 10 μmols of thiophenol and 25 μmols of 2-carboxythiophenol, to synthesize a sulfide derivative which was a stable precursor of the vinyl compound. Further reacting therewith an active ester N-succinimidyl 3-(2-pyridylthio)propionate (SPDP) having a protected thiol group in a phosphate buffer, (pH 7.5) containing 1 mM ethylenediamine tetraacetate (EDTA). Then reducing the reaction product with dithiothreitol, a) functional oligonucleotide having a thiol group at 3' terminal was synthesized. Thus obtained modified oligonucleotide having a thiol group at 3' terminal (0.2 μmol) was reacted with the PEG derivative in a phosphate buffer (pH 8.0) for 5 hours, to produce the intended PEG-functional oligonucleotide conjugate formed by conjugation of the PEG with the functional oligonucleotide at a high effectivity (see, FIG. 1). Also the following reaction schemes can be referred to.

R = Me
R = Ph
R = 2-carboxyl-Ph

R = Me
R = Ph
R = 2-carboxyl-Ph

EXAMPLE 2

Preparation of Polyion Complex (PIC) Micelle Formed of PEG-Functional Oligonucleotide Conjugate and Polylysine PEG-functional oligonucleotide conjugate (60 nmols) and 144 nmols of polylysine (average degree of polymerization=100) were each dissolved in 10 mM tris-HCl buffer (pH 7.4), and from the solutions dust was removed by filtration through filter. Then these solutions were mixed such that the ratio of positive charge of the polylysine to negative charge of the PEG-functional oligonucleotide conjugate became 1 (N/P=1). Further 10 mM tris-HCl buffer (pH 7.4, 0.3M NaCl) of the same quantity to that of the liquid mixture was added, followed by 12 hours' standing to form a PIC micelle.

EXAMPLE 3

Antisense Effect of PIC Micelle Formed of PEG-Functional Oligonucleotide Conjugate and Polylysine A 24-well polystyrene cell culture plate (Falcon Co.) was seeded with human liver cancer cells (Huh 7 cell) at a rate of 5×104 cells/well, cultured for 24 hours, and the cells were transfected with reporter genes of firefly [*Luciola cruciata*] luciferase plasmid DNA (pGL3, 0.084 μg/well, Promega Co.), and sea kidney [*Renilla reinformis*] luciferase plasmid DNA (pRL-TK, 0.75 μg/well, Promega Co.), using Lipofect AMINE (1.22 μL/well, Invitrogen Co.) which is a commercialized gene-insertion reagent. Then the PIC micelle solution having the antisense sequence to the firefly luciferase genes (which was prepared in Example 2), a solution of the PEG-functional oligonucleotide conjugate alone, and a solution of the functional oligonucleotide alone of each prescribed amount were added (the amount as would make 5 μM conjugate as converted to culture medium concentration), to have each of the solutions contact with the cells for 24 hours. After changing the culture medium, the cultivation was continued for further 24 hours. Then the cells were recovered and representations of the two reporter genes were measured with Dual Luciferase Reporter Assay System (Promega Co.) to evaluate the antisense effect (n=3).

For comparison, antisense effects of PIC micelle formed of PEG-antisense DNA conjugate and polylysine, PEG-antisense DNA conjugate alone and antisense DNA alone were also evaluated under the same conditions as used in Example 3.

Figure 2:
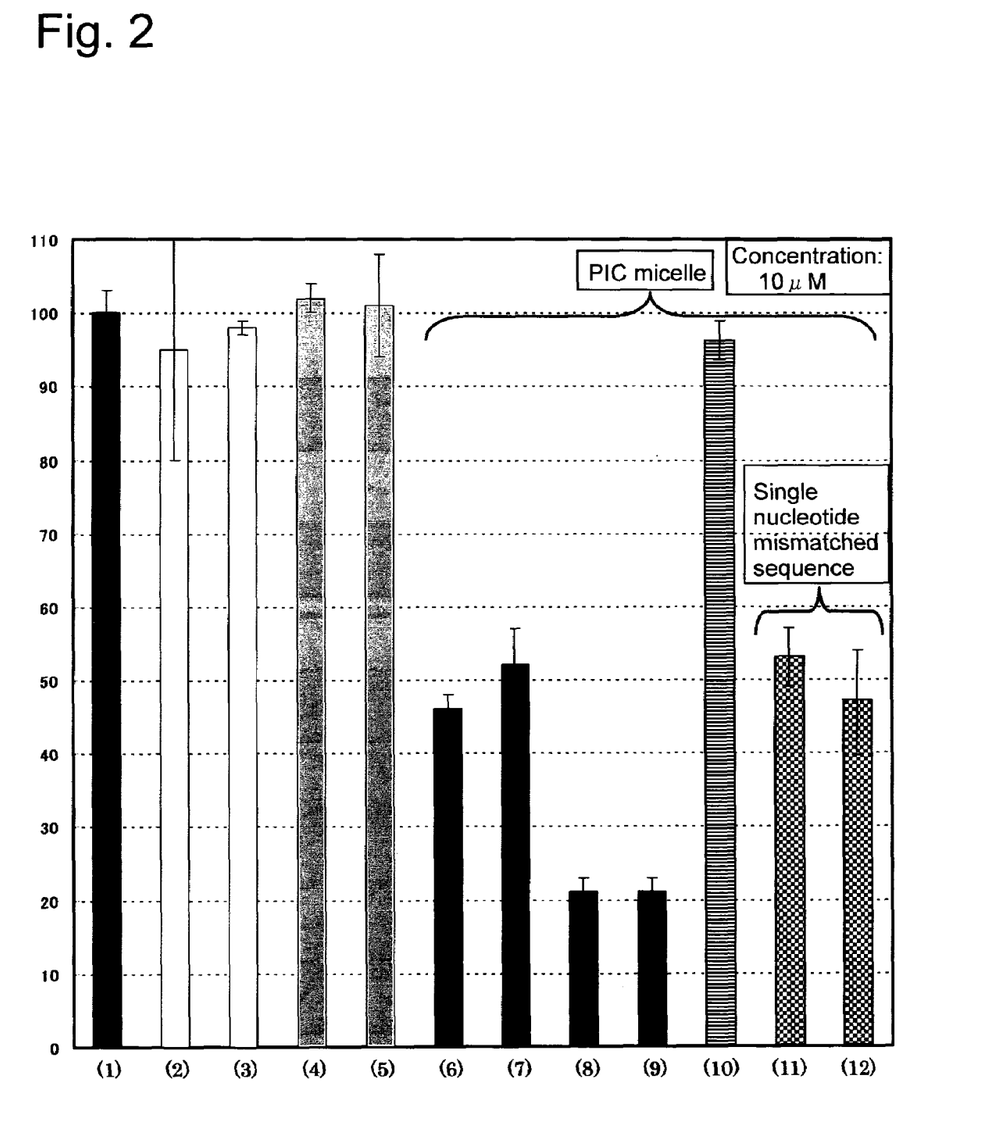

The results were as shown in FIG. 2, which confirmed that control (1), antisense DNA alone (2), SPh functional oligonucleotide alone (3), PEG antisense DNA conjugate alone (4) and PEG-Sph functional oligonucleotide conjugate alone (5) showed entirely no antisense effect. On the other hand, those PIC micelles were confirmed to exhibit antisense effect. Specifically, the PIC micelle (8) of PEG-functional oligonucleotide conjugate having SMe structure (antisense effect of about 80%) and the PIC micelle (9) of PEG-functional oligonucleotide conjugate having SPh structure (antisense effect of about 80%) were confirmed to exhibit higher antisense effect than the PIC micelle (6) of PEG-antisense DNA conjugate (antisense effect of about 55%).

The fact that the PIC micelle (10) of PEG-functional oligonucleotide conjugate of SPh structure having random base sequence (irrelevant to firefly luciferase genes) showed no antisense effect indicates that the above-confirmed antisense effects were specific for the target genes.

Furthermore, it was confirmed: while the antisense effect of the PEG-antisense DNA conjugate PIC micelle (11) having single nucleotide mismatched sequence was approximately equivalent to that of the PIC micelles not having any single nucleotide mismatched sequence, that of the PIC micelle (12) of PEG-functional oligonucleotide conjugate having SPh structure containing single nucleotide mismatched sequence markedly decreased from the antisense effect of the PIC micelles having no single nucleotide mismatched sequence. Thus it is made clear that this PIC micelle (9) of PEG-functional oligonucleotide conjugate having SPh structure has high sequence recognition.

Antisense effect of the PIC micelle formed of PEG-functional oligonucleotide conjugate of SPh structure having lactose (ligand) and polylysine was also evaluated under the same conditions as used in Example 3

Figure 3:
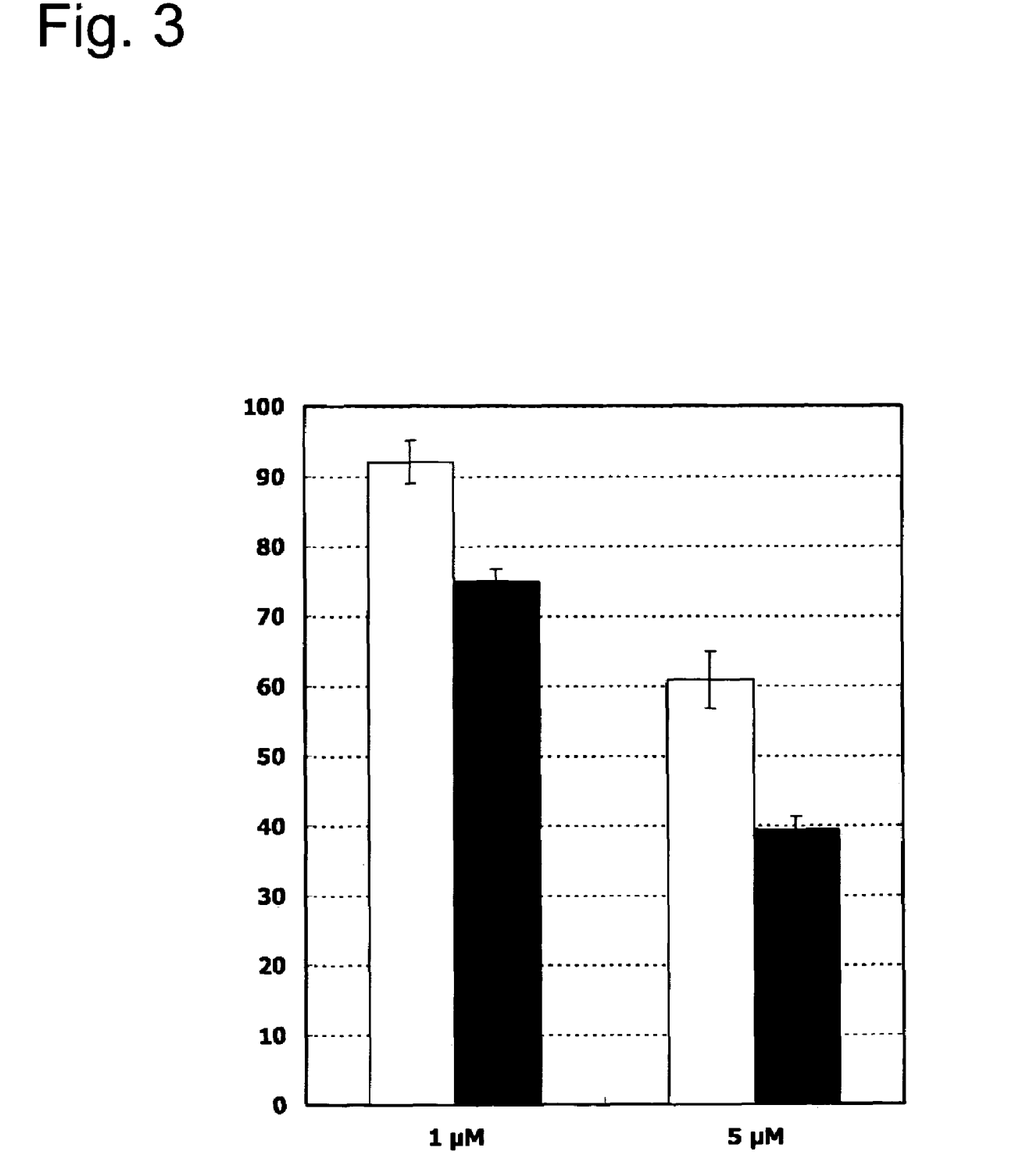
FIG. 3 is a graph showing the antisense effect of PIC micelle according to the present invention, which is formed of a conjugate having a ligand (lactose) and polylysine. The axis of ordinates stands for representation of firefly luciferase/representation of sea kidney luciferase (%) and the axis of abscissae, PEG-functional oligonucleotide conjugate. The solid black bars show the results of the PIC micelle of lactose-containing SPh conjugate, and the blank bars, those of PIC micelle of lactose-free SPh conjugate.

The results were as shown in FIG. 3. At any of the concentration levels of 1 μM and 5 μM, the PIC micelle of PEG-functional oligonucleotide conjugate of SPh structure having lactose (solid black bars) was confirmed to exhibit higher antisense effect.

INDUSTRIAL APPLICABILITY

PEG-functional oligonucleotide conjugates according to the present invention can form stable PIC micelles particularly with polycation, exhibit target specificity, and inhibit expression of various disease-inducing genes. They therefore are useful for therapy of corresponding diseases, e.g., useful in the art of making medicines.

The invention claimed is:

1. A conjugate of oligonucleotide with poly(ethylene oxide) which is expressed by a formula (A):

$$\text{FuNT-}L_1\text{-}L_2\text{-PEG} \qquad (A)$$

in which FuNT stands for the residue of a functional oligonucleotide bound to $L_1$-$L_2$-PEG via a phosphate ester bond at 3' or 5' hydroxyl terminal of ribose or 2-deoxyribose, wherein the functional oligonucleotide
a) is composed of an oligonucleotide sequence which either is complementary to the nucleotide sequence participating in expression of target genes, or hybridizes with the nucleotide sequence under stringent condition; and which has, at 6-position of at least one 2-aminopurine ring present in the oligonucleotide sequence, a group of the formula —$CH_2CH_2S(O)nR$ (wherein n stands for an integer of 0-2; and R stands for $C_1$-$C_6$ alkyl optionally substituted with oxy (=O), cyano or carboxy; or phenyl optionally substituted with oxy (=O), cyano, nitro, carboxy, $C_1$-$C_6$ alkyl or halo); or
b) is complementary to the nucleotide sequence participating in expression of the target genes and the phosphate moiety of each nucleotide therein is selected from the group consisting of phosphorothioate, phosphoroamidate and 2'-O-methylphosphate;

$L_1$ stands for an alkylene group of 3-30 in total atom number, which may be interrupted with oxygen atom or sulfur atom at one, two or more places;

$L_2$ stands for a linking group cleavable under physiological conditions; and

PEG stands for poly(ethylene oxide) group carrying at the $L_2$-binding terminal hydrogen atom, alkyl group, aralkyl group, functional group or ligand residue, optionally via a linking group; and
wherein the oligonucleotide is an oligodeoxynucleotide containing 10-50 nucleotides.

2. A conjugate of oligonucleotide with poly(ethylene oxide) which is expressed by a formula (A):

$$\text{FuNT-}L_1\text{-}L_2\text{-PEG} \qquad (A)$$

in which FuNT stands for the residue of a functional oligonucleotide bound to $L_1$-$L_2$-PEG via a phosphate ester bond at 3' or 5' hydroxyl terminal of ribose or 2-deoxyribose, wherein the functional oligonucleotide is composed of an oligonucleotide sequence which either is complementary to the nucleotide sequence participating in expression of target genes, or hybridizes with the nucleotide sequence under stringent condition; and which has, at 6-position of at least one 2-aminopurine ring present in the oligonucleotide sequence, a group of the formula —$CH_2CH_2S(O)nR$ (wherein n stands for an integer of 0-2; and R stands for $C_1$-$C_6$ alkyl optionally substituted with oxy (=O), cyano or carboxy; or phenyl optionally substituted with oxy (=O), cyano, nitro, carboxy, $C_1$-$C_6$ alkyl or halo);

$L_1$ stands for an alkylene group of 3-30 in total atom number, which may be interrupted with oxygen atom or sulfur atom at one, two or more places;

$L_2$ stands for a linking group cleavable under physiological conditions; and

PEG stands for poly(ethylene oxide) group carrying at the $L_2$-binding terminal hydrogen atom, alkyl group, aralkyl group, functional group or ligand residue, optionally via a linking group.

3. The conjugate as set forth in claim 2, in which the functional oligonucleotide is an antisense deoxyoligonucleotide, at least one 2-deoxyguanosine in the deoxyoligonucleotide having a group of a formula —$CH_2CH_2S(O)_nR'$ (wherein n stands for an integer of 0-2, and R' stands for methyl or phenyl), and the poly(ethylene oxide) has a number-average molecular weight of 200-30,000.

4. The conjugate as set forth in claim 1, in which the linking group in $L_2$, which is cleavable under physiological conditions, has on its main chain an ester bond (—COO—) or disulfide bond (—SS—).

5. The conjugate as set forth in claim 1, in which the -PEG is represented by a formula $$-(CH_2CH_2O)_n\text{-}L_3\text{-}X$$

in the formula, $L_3$ is single bond or a linking group selected from those alkylene or linking groups as defined for $L_1$ or $L_2$, X is hydrogen; or a functional group selected from the group consisting of alkyl, aralkyl, hydroxyl, formyl, acetalized formyl, amino, protected amino, maleimide, carboxyl and protected carboxyl, or a ligand which is bound via such a functional group and n is an integer of 5-500.

6. A complex comprising a polymer containing polycationic segment and a conjugate of oligonucleotide with poly(ethylene oxide) which is expressed by a formula (A):

$$\text{FuNT-}L_1\text{-}L_2\text{-PEG} \qquad (A)$$

in which FuNT stands for the residue of a functional oligonucleotide bound to $L_1$-$L_2$-PEG via a phosphate ester bond at 3' or 5' hydroxyl terminal of ribose or 2-deoxyribose, wherein the functional oligonucleotide
a) is composed of an oligonucleotide sequence which either is complementary to the nucleotide sequence participating in expression of target genes, or hybridizes with the nucleotide sequence under stringent condition; and which has, at 6-position of at least one 2-aminopurine ring present in the oligonucleotide sequence, a group of the formula —$CH_2CH_2S(O)nR$ (wherein n stands for an integer of 0-2; and R stands for $C_1$-$C_6$ alkyl optionally substituted with oxy (=O), cyano or carboxy; or phenyl optionally substituted with oxy (=O), cyano, nitro, carboxy, $C_1$-$C_6$ alkyl or halo); or
b) is complementary to the nucleotide sequence participating in expression of the target genes and the phosphate moiety of each nucleotide therein is selected from the group consisting of phosphorothioate, phosphoroamidate and 2'-O-methylphosphate;

$L_1$ stands for an alkylene group of 3-30 in total atom number, which may be interrupted with oxygen atom or sulfur atom at one, two or more places;

$L_2$ stands for a linking group cleavable under physiological conditions; and

PEG stands for poly(ethylene oxide) group carrying at the $L_2$-binding terminal hydrogen atom, alkyl group, aralkyl group, functional group or ligand residue, optionally via a linking group.

7. The complex as set forth in claim 6, in which the polymer containing polycationic segment is a homopolymer or a block copolymer containing the polycationic segment and poly(ethylene oxide) segment.

8. The complex as set forth in claim 6, in which the polycationic segment in the homopolymer is selected from the group consisting of polylysine, polyethyleneimine, poly2-(N,N-di-$C_{1-3}$ alkylaminoethyl)methacrylate, oligoarginine, tat and KALA.

9. The complex as set forth in claim 6, which forms a poly ion complex micelle formed of a shell constituted mainly of poly(ethylene oxide) chain and a core constituted mainly of a functional oligonucleotide in an aqueous medium.

10. The complex as set forth in claim 6, in which the functional oligonucleotide is an antisense deoxyoligonucleotide, at least one 2-deoxyguanosine in the deoxyoligonucleotide having a group of a formula —$CH_2CH_2S(O)_nR'$ (wherein n stands for an integer of 0-2, and R' stands for methyl or phenyl) at its 6-position.

11. The conjugate as set forth in claim 3, in which the -PEG is represented by a formula —$(CH_2CH_2O)_n$—$L_3$—X in the formula, $L_3$ is single bond or a linking group selected from those alkylene or linking groups as defined for $L_1$ or $L_2$, X is hydrogen; or a functional group selected from the group consisting of alkyl, aralkyl, hydroxyl, formyl, acetalized formyl, amino, protected amino, maleimide, carboxyl and protected carboxyl, or a ligand which is bound via such a functional group and n is an integer of 5-500.

12. The conjugate as set forth in claim 4, in which the -PEG is represented by a formula —$(CH_2CH_2O)_n$—$L_3$—X in the formula, $L_3$ is single bond or a linking group selected from those alkylene or linking groups as defined for $L_1$ or $L_2$, X is hydrogen; or a functional group selected from the group consisting of alkyl, aralkyl, hydroxyl, formyl, acetalized formyl, amino, protected amino, maleimide, carboxyl and protected carboxyl, or a ligand which is bound via such a functional group and n is an integer of 5-500.

13. The conjugate as set forth in claim 2, in which the linking group in $L_2$, which is cleavable under physiological conditions, has on its main chain an ester bond (—COO—) or disulfide bond (—SS—).

14. The conjugate as set forth in claim 2, in which the -PEG is represented by a formula —$(CH_2CH_2O)_n$—$L_3$—X in the formula, $L_3$ is single bond or a linking group selected from those alkylene or linking groups as defined for $L_1$ or $L_2$, X is hydrogen; or a functional group selected from the group consisting of alkyl, aralkyl, hydroxyl, formyl, acetalized formyl, amino, protected amino, maleimide, carboxyl and protected carboxyl, or a ligand which is bound via such a functional group and n is an integer of 5-500.

* * * * *